United States Patent [19]

Baxter et al.

[11] 4,410,548

[45] Oct. 18, 1983

[54] PROPANOLAMINE DERIVATIVES

[75] Inventors: Andrew J. G. Baxter, Shepshed; Malcolm Myers, Hull, both of England

[73] Assignee: Reckitt & Colman Products Limited, London, England

[21] Appl. No.: 277,610

[22] Filed: Jun. 26, 1981

[30] Foreign Application Priority Data

Jul. 9, 1980 [GB] United Kingdom ................ 8022464

[51] Int. Cl.$^3$ .......................................... A61K 31/135
[52] U.S. Cl. .................................. 424/330; 564/349; 549/9; 549/23
[58] Field of Search ............... 564/349; 424/330, 275; 549/9, 23

[56] References Cited

U.S. PATENT DOCUMENTS 3,723,524 3/1973 Augstein et al. .................... 564/349
4,067,904 1/1978 Comer et al. ........................ 564/349
4,165,384 8/1979 Carlsson et al. .................... 564/349

FOREIGN PATENT DOCUMENTS 1245148 9/1971 United Kingdom ................ 564/165
1544872 4/1979 United Kingdom .

OTHER PUBLICATIONS

Drugs of the Future, vol. V, No. 2, (1980), pp. 87–89.
Drugs of the Future, vol. 1, (1976) pp. 38–42.
Augstein et al., J. Med. Chem., vol. 16, No. 11 (1973) pp. 1245–1251.
Smith, et al., J. Med. Chem., vol. 20(12) 1653 (1977).

Primary Examiner—Thomas G. Wiseman
Assistant Examiner—Frederick W. Pepper
Attorney, Agent, or Firm—Bacon & Thomas

[57] ABSTRACT

Propanolamine derivatives of the formula:

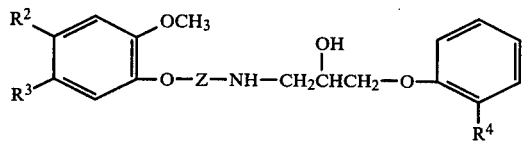

wherein
$R^2$ is $CH_3SO$ or $CH_3SO_2$;
$R^3$ is hydrogen, methyl or methoxy; or
$R^2$ and $R^3$ are together —$S(O)_m(CH_2)_4$— when S is attached at $R^2$ or —$(CH_2)_nS(O)_m$— when S is attached at $R^3$ (where m=1 or 2 and n=3 or 4);
$R^4$ is hydrogen or alkyl $C_{1-4}$;
Z is —$(CH_2)_2$— or

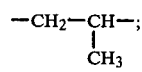

and their non-toxic salts.

Processes for the preparation and pharmaceutical compositions thereof. The compounds exhibit both β-adrenoreceptor antagonist activity and vasodilator activity and are indicated for use in the treatment of hypertension.

10 Claims, No Drawings

PROPANOLAMINE DERIVATIVES

This invention relates to propanolamine derivatives their non-toxic salts, processes for their preparation and pharmaceutical compositions of the derivatives or their salts.

British Pat. No. 1,245,148 discloses and claims compounds of the formula

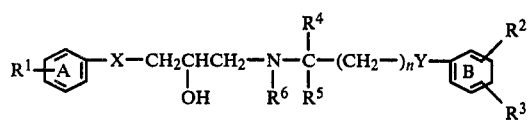

where
- $R^1$ represents hydrogen, halogen, or a lower alkyl, phenyl, lower alkoxy or phenyl-substituted lower alkyl group;
- $R^2$ represents hydrogen, or up to 2 halogen, lower alkyl or lower alkoxy substituents;
- $R^3$ represents an electron-withdrawing polar substituent;
- $R^4$ and $R^5$ each represent hydrogen or a lower alkyl group;
- $R^6$ represents hydrogen or a lower alkyl, lower alkanoyl or benzyl group; either of the benzene rings A and B may be optionally substituted further by a —CH=CH—CH=CH— radical to form a naphthyl group;
- X represents oxygen or sulphur;
- and either Y represents oxygen, sulphur, or a sulphinyl, sulphonyl or imino group and n is 1, 2 or 3; or Y represents a direct link and n is 0, 1, 2, 3 or 4;
the carboxylic acid esters and aldehyde condensation products of such compounds, and their pharmaceutically acceptable acid addition salts. Particularly preferred compounds are those in which $R^3$ is an unsubstituted carbamoyl group in the 2-position or the 4-position on the phenyl group, and when such group is in the 2-position then $R^2$ is a methyl or methoxy group in the 4-, 5- or 6-position on the phenyl group. The compounds are stated to have the property of blocking the β-adrenergic receptors and are useful in the curative or prophylactic treatment of cardiac conditions, such as angina pectoris and cardiac arrhythmias, and in the treatment of hypertension.

The patent further states that electron-withdrawing polar substituents are those which contain a polar group with its electropositive atom adjacent to the phenyl ring, including those in which the polar group is separated from the phenyl ring by a methylene or ethylene group. Polar groups including the carbonyl, sulphonyl, sulphinyl, cyano, azido, nitro and trihalomethyl groups, and $R^3$ in the above formula may therefore be, for example, a carboxy, lower alkoxycarbonyl, formyl, lower alkanoyl, carbamoyl, sulpho, sulphino, alkoxysulphonyl, alkoxysulphinyl, sulphamoyl, cyano, azido, nitro or trifluoromethyl group, or any such group separated from the phenyl ring by a methylene or ethylene group, e.g. a carboxymethyl, lower-alkoxycarbonyl-methyl, formylmethyl, acetonyl and other lower-alkanoyl-methyl radicals, carbamoyl-methyl, sulphomethyl, sulphinomethyl, lower-alkoxysulphonyl (and sulphinyl)-methyl, sulphamoylmethyl and cyanomethyl, as well as the corresponding polar-substituted ethyl radicals.

According to the present invention there are provided compounds of the formula

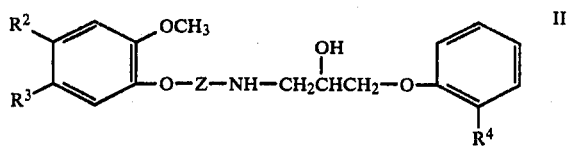

wherein
- $R^2$ is $CH_3SO$ or $CH_3SO_2$;
- $R^3$ is hydrogen, methyl or methoxy; or
- $R^2$ and $R^3$ are together —$S(O)_m(CH_2)_4$— when S is attached at $R^2$ or —$(CH_2)_nS(O)_m$— when S is attached at $R^3$ (where m=1 or 2 and n=3 or 4);
- $R^4$ is hydrogen or alkyl $C_{1-4}$;
- Z is —$(CH_2)_2$— or

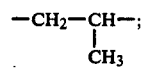

and their non-toxic salts.

In an aspect of the invention there are provided compounds of the formula

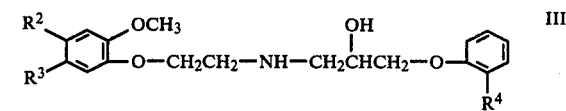

wherein
- $R^2$ is $CH_3SO$ or $CH_3SO_2$;
- $R^3$ is hydrogen, methyl or methoxy; or
- $R^2$ and $R^3$ are together —$S(O)_m(CH_2)_4$— when S is attached at $R^2$ or —$(CH_2)_nS(O)_m$— when S is attached at $R^3$ (where m=1 or 2 and n=3 or 4);
- $R^4$ is hydrogen or methyl; and their non-toxic salts.

It will be appreciated that the compounds of formula II and III contain at least one asymmetric centre (the carbinol carbon atom). There are additional asymmetric centres in those compounds in which $R^2$ or $R^2$ together with $R^3$ contain a SO group, or where Z is

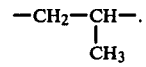

It is to be understood that the invention includes the stereochemically isomeric forms either individually or as mixtures of two or more.

The invention also includes pharmaceutical compositions comprising a compound of formula II or formula III or a non-toxic salt thereof, together with a pharmaceutically acceptable diluent or carrier.

Examples of non-toxic salts are those with inorganic acids such as hydrochloric, sulphuric or phosphoric acid or organic acids such as acetic, propionic, malonic, oxalic, succinic, fumaric, maleic, tartaric, citric or cinnamic acid.

The compounds of the invention exhibit pharmacological activity, in particular they have both β-adrenoreceptor antagonist activity and vasodilator activity as indicated by animal testing and are therefore indicated for use in man in the treatment of hypertension.

The compounds of formula II in which Z is —(CH₂)₂— may be prepared from an amide of formula

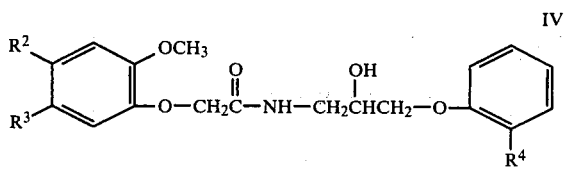
IV wherein R², R³ and R⁴ are as hereinbefore defined, by reduction with sodium borohydride/acetic acid or with borane/tetrahydrofuran complex, provided that when R² or R² together with R³ contains a SO group reduction is carried out with sodium borohydride/acetic acid.

The amide of formula IV may be prepared by reaction of an alkali metal salt of a phenol of formula

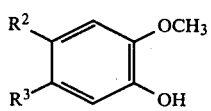
V with a haloacetamide of the formula

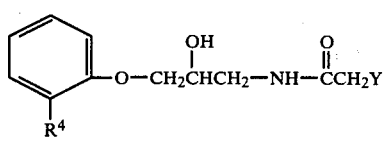
VI wherein R², R³ and R⁴ are as hereinbefore defined and Y is chlorine or bromine. Conveniently the amide is formed by adding one equivalent of a strong base such as sodium hydride to a solution of the phenol in an inert dry solvent such as dimethylformamide and thereafter reacting with the haloacetamide at a temperature in the range 80° to 120° C. With the amides of formula IV in which R² or R² together with R³ contain a SO group the use of borane/tetrahydrofuran complex as the reducing agent leads to reduction not only of the amide group to amine but also of the SO group to sulphide. In the case of the compounds of formula II in which R² or R² together with R³ contain a SO₂ group it has been found to be particularly convenient to prepare the analogous amides IV in which R² or R² together with R³ contain a SO or sulphide group and to oxidise with at least one or two molar equivalents respectively of a peracid such as peracetic acid or m-chloroperbenzoic acid to form the analogous amides containing a sulphone group which are thereafter reduced to the amines.

The haloacetamides of formula VI may conveniently be prepared by treating an amine of formula

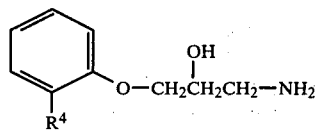
VII wherein R⁴ is as hereinbefore defined, (as free base or HCl salt) in methylene chloride at 0° to 25° C. with a molar equivalent of haloacetyl halide (such as chloracetyl chloride) in the present of a half molar equivalent of N,N,N',N'-tetramethylethylenediamine (or a molar equivalent if the HCl salt of the amine of formula VII is used).

The compounds of formula II in which R² or R² together with R³ contain a SO group may also be prepared from the analogous compounds of formula II in which R² or R² together with R³ contain a sulphide group by treatment with a molar equivalent of a peracid such as peracetic acid or m-chloroperbenzoic acid.

As mentioned above reduction of amides of formula IV in which R² or R² together with R³ contain a SO group with borane/tetrahydrofuran complex leads to simultaneous reduction of amide to amine and SO to sulphide. For the compounds of formula II in which Z is —(CH₂)₂—, and R² or R² together with R³ contain a SO group it has been found to be particularly convenient to reduce the analogous amide of formula IV in this manner and then to oxidise the resultant amine-sulphide to amine-sulphoxide.

The compounds of formula II wherein Z, R², R³ and R⁴ are as hereinbefore defined and the analogous sulphide compounds in which R² or R² together with R³ contain a sulphide group, are also preparable by a variety of methods including:

(1) Reaction of a halo compound of the formula

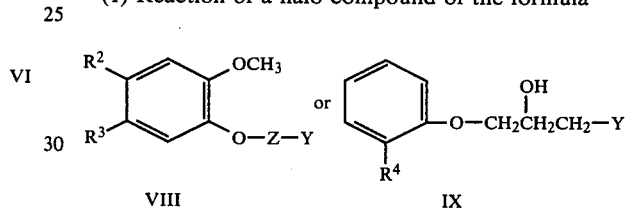
VIII    IX with respectively an amine of formula VII or formula X

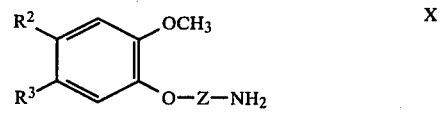
X wherein Y is halogen especially bromine or chlorine. Preferably the reaction is carried out at 20° to 80° C. in a suitable solvent such as ethanol either in the presence of an excess of the amine or in equimolar proportions in the presence of an inorganic base such as sodium bicarbonate.

(2) Reaction of an epoxy compound of the formula

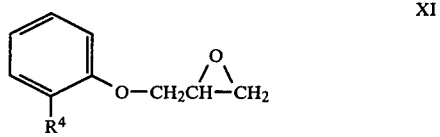
XI with an amine of formula X. Conveniently the reaction is carried out in a suitable solvent such as methanol at a temperature in the range 20° to 60° C.

(3) Reaction of an aldehyde or ketone of the formula

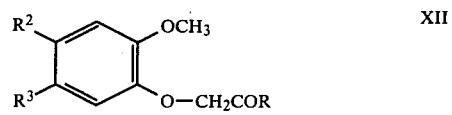
XII wherein R is hydrogen or methyl, with an amine of formula VII and the resultant Schiff's base is thereafter reduced with sodium borohydride or catalytically with hydrogen in the presence of a platinum or palladium catalyst.

The amines of formula X may be prepared by standard methods. A particularly convenient method for preparing those compounds in which Z is —(CH$_2$)$_2$— involves reaction of the analogous phenols of formula V with an excess (20–50 molar equivalents) of aziridine in ethanol at 60° to 100° C.

The analogous compounds of those of formula II wherein Z is —(CH$_2$)$_2$—, R$^4$ is as hereinbefore defined and R$^2$ or R$^2$ together with R$^3$ contain a sulphide group may also be prepared by reacting an analogous halo sulphide compound of formula VIII, wherein Y is bromine, with an oxazolidinone of formula

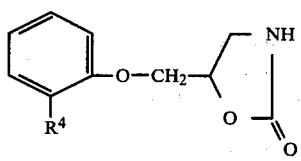

XIII wherein R$^4$ is as hereinbefore defined in the presence of 1 to 3 molar equivalents of aqueous sodium hydroxide and of 2–20% (by weight) of benzyltriethylammonium chloride in dichloromethane at 20°–45°, and then hydrolysing the resultant product in an alkanol such as ethanol with 2 to 5 fold excess of aqueous sodium or potassium hydroxide at 60°–100°.

The invention is illustrated by the following Examples in which temperatures are in degrees Celsius.

The various compounds and intermediates were examined by thin layer chromatography (t.l.c.) on silica gel plates (Merck, Kieselgel 60 F$_{254}$) using the following systems, where ratios are volume/volume:

C chloroform
E diethyl ether
1G chloroform, methanol 19:1
1E chloroform, methanol 4:1

EXAMPLE 1

1-[2-(2-Methoxy-5-methyl-4-methylsulphinylphenoxy)ethylamino]-3-(2-methylphenoxy)propan-2-ol oxalate salt (a)
2-(2-Methoxy-5-methyl-4-(methylthio)phenoxy)ethylamine 2-Methoxy-5-methyl-4-(methylthio)phenol (3.8 g) in ethanol (50 ml) was stirred at reflux for 48 hours during which time aziridine (6×5 ml) was added portionwise. The solvent was evaporated and the residue was dissolved in 2 N aqueous sodium hydroxide (50 ml) and chloroform (50 ml). The organic layer was washed with water (50 ml) and then extracted with 2 N hydrochloric acid (50 ml). The acidic layer was basified with solid sodium hydrogen carbonate and extracted with chloroform (50 ml). The organic layer was washed with water (50 ml), dried (Na$_2$SO$_4$) and evaporated under reduced pressure. Column chromatography of the resulting solid on silica gel eluting with chloroform/methanol mixtures (gradient 0 to 5% v/v methanol) gave the thioamine (2.3 g) as an off-white solid, m.p. 68°–70°.

(b)
2-(2-Methoxy-5-methyl-4-methylsulphinylphenoxy)ethylamine

The above thioamine (1.7 g) was dissolved in chloroform (20 ml), treated with an excess of ethereal hydrogen chloride and the solvent removed in vacuo to give a solid which was dissolved in water (30 ml). Sodium periodate (1.53 g) was added and the resulting solution was stirred for 3 hours. The solution was basified with solid sodium hydrogen carbonate and extracted copiously with methylene chloride. The combined organic extracts were dried (Na$_2$SO$_4$) and the solvent removed in vacuo to give the sulphinylamine (1.4 g) as a hygroscopic gum.

A sample, purified by column chromatography on silica gel eluting with methylene chloride/methanol mixtures (gradient 0 to 5% v/v methanol) had m.p. 67°–69°.

(c)
1-[2-(2-Methoxy-5-methyl-4-methylsulphinylphenoxy)ethylamino]-3-(2-methylphenoxy)propan-2-ol oxalate salt The above sulphinylamine (2.42 g) was dissolved in methanol (25 ml) and 3-(2-methylphenoxy)-1,2-epoxypropane (0.82 g) in methanol (5 ml) was added. A second portion of the epoxide (0.82 g) was added after 6 hours and the resulting solution stirred overnight. The solution was evaporated to dryness and the residue was chromatographed on a column of silica gel eluting with chloroform/methanol mixtures (gradient 0 to 5% v/v methanol) to give the amine as an oil. The oil was taken up in methanol and oxalic acid (equimolar) was added. Evaporation of the methanol in vacuo and crystallisation from ethanol gave the amine oxalate salt (0.69 g) as colourless crystals, m.p. 149°–151°. Found: C, 54.8; H, 6.1; N, 2.7 C$_{21}$H$_{29}$NO$_5$S.C$_2$H$_2$O$_4$.½H$_2$O requires C, 54.5; H, 6.4; N, 2.7%.

EXAMPLE 2

1-[2-(2-Methoxy-5-methyl-4-methylsulphinylphenoxy)ethylamino]-3-(2-methylphenoxy)propan-2-ol oxalate salt (a)
1-(2-Chloroacetamido)-3-(2-methylphenoxy)-propan-2-ol A mixture of 1-amino-3-(2-methylphenoxy)propan-2-ol hydrochloride (21.8 g) and N,N,N',N'-tetramethylethylenediamine (11.6 g) was stirred for 30 minutes in dry methylene chloride (200 ml). Chloroacetyl chloride (11.3 g, 7.6 ml) was added to the solution at 0° over 30 minutes. After a further 30 minutes the solution was filtered and the solvent removed under reduced pressure. Purification by column chromatography on silica gel eluting with methylene chloride/methanol mixtures (gradient 0 to 3% v/v methanol) gave the chloroamide as an off-white solid (21.5 g). R$_f$E 0.66.

(b) 2-Methoxy-5-methyl-4-methylsulphinylphenol (i) Sodium hydride (5.25 g of a 50% w/w dispersion in oil) was added to a solution of ethanethiol (12.5 ml) in dry dimethylformamide (100 ml) at 0° with stirring. After evolution of hydrogen had ceased additional ethanethiol (5 ml) was added followed by 1,2-dimethoxy-4-methyl-5-methylsulphinybenzene (21.5 g). The mixture was heated at 100°–120° for 4 hours and then cooled. The solid was filtered off, washed with diethyl ether and then dissolved in water (150 ml). The aqueous solution was washed with diethyl ether (100 ml) and then made acidic with conc. hydrochloric acid. This solution was saturated with solid sodium chloride and then extracted with chloroform (3×150 ml). The combined chloroform extracts were dried (Na$_2$SO$_4$) and the solvent evaporated to yield a solid. Recrystallisation from chloroform (70 ml) and 60°-80° petroleum ether (30 ml) gave 2-methoxy-5-methyl-4-methylsulphinylphenol (9 g) as colourless crystals m.p. 165°-166°. Column chromatography of the liquors on silica gel eluting with chloroform/methanol mixtures (gradient 0 to 2% v/v methanol) gave 2-methoxy-4-methyl-5-methylsulphinylphenol (0.35 g) as colourless crystals m.p. 148°-150°.

(ii) 10% v/v Aqueous hydrogen peroxide (27 ml) was added to 2-methoxy-5-methyl-4-(methylthio)phenol (1.72 g) in glacial acetic acid (15 ml). After 24 hours the acetic acid was neutralised with 2 N aqueous sodium hydroxide and the product was extracted into methylene chloride (100 ml). The organic extract was washed with 10% w/v aqueous sodium sulphite solution and water, dried (Na$_2$SO$_4$) and the solvent was removed in vacuo. Recrystallisation from ethanol/diethyl ether gave 2-methoxy-5-methyl-4-methylsulphinylphenol (0.16 g) as colourless crystals m.p. 166°-168° (identical to that prepared in (i) above).

(c)
1-[2-(2-Methoxy-5-methyl-4-methylsulphinylphenoxy)acetamido]-3-(2-methylphenoxy)propan-2-ol Sodium hydride (3.7 g) of a 50% w/w dispersion in oil was added with stirring to 2-methoxy-5-methyl-4-methylsulphinylphenol (15 g) in dry dimethylformamide (250 ml). After the hydrogen had evolved, the above chloroamide (20 g) was added and the mixture was then heated to 100° for 1½ hours. The mixture was cooled, filtered and the solvent was removed in vacuo. Ethyl acetate (300 ml) was added to the residue and, after standing for 1½ hours, the precipitate was filtered off. The ethyl acetate solution was reduced in volume to about 100 ml under reduced pressure cooled and filtered. The resultant solid was washed with ethyl acetate and diethyl ether and then dried in vacuo to give the amide (23.5 g).

A sample purified by column chromatography on silica gel eluting with methylene chloride/methanol mixtures (gradient 0 to 3% v/v methanol) and then crystallisation from ethyl acetate had m.p. 106°-108°.

(d)
1-[2-(2-Methoxy-5-methyl-4-methylsulphinylphenoxy)ethylamino]-3-(2-methylphenoxy)propan-2-ol oxalate salt Acetic acid (33 ml) in dry tetrahydrofuran (50 ml) was added dropwise with stirring to a mixture of the above amide (23.5 g), and sodium borohydride (22 g) in dry tetrahydrofuran (500 ml) at 10°. The mixture was heated at reflux for 3½ hours, cooled and filtered. The collected solid was added to the residue obtained from the evaporation of the solvent under reduced pressure from the filtrate, and water (500 ml) was added to the mixture. The aqueous solution was extracted with chloroform (2×500 ml). The chloroform extracts were dried (Na$_2$SO$_4$) and evaporated under reduced pressure. 2 N Hydrochloric acid (50 ml) was added, followed by the careful addition of conc. hydrochloric acid (30 ml). After 30 minutes chloroform (200 ml) and water (100 ml) were added and the aqueous layer made basic using solid sodium hydroxide. The organic layer was separated and the aqueous layer was re-extracted with chloroform (200 ml). The combined organic extracts were dried (Na$_2$SO$_4$) and the solvent was removed in vacuo. The residue was dissolved in methanol (50 ml) and then a solution of oxalic acid (4.55 g) in methanol (20 ml) was added. The resultant solid was collected and recrystallised from ethanol (80 ml) to give the amine oxalate salt (10.4 g) as a colourless solid, m.p. 149°-151° (identical to that prepared in Example 1).

EXAMPLE 3

1-[2-(2-Methoxy-5-methyl-4-methylsulphinylphenoxy)ethylamino]-3-(2-methylphenoxy)-propan-2-ol oxalate salt Borane-tetrahydrofuran complex (15 ml of 1 M solution in tetrahydrofuran) was added dropwise with stirring at 0° to the amide of Example 2(c) (2.0 g) in dry tetrahydrofuran (35 ml). After heating for 2 hours at reflux, the mixture was cooled and 6 N hydrochloric acid (10 ml) was added. Tetrahydrofuran (40 ml) was distilled off at atmospheric pressure and then water (15 ml) was added to the cooled solution. The solution was basified with solid sodium hydroxide and extracted with chloroform (2×40 ml). The combined organic extracts were dried (Na$_2$SO$_4$) and the solvent was removed under reduced pressure. The residue was dissolved in methanol (30 ml), cooled at 0°, and then, with vigorous stirring, peracetic acid (4.75 ml of a 1 M solution in methanol freshly made from 40% w/w peracetic acid in acetic acid) was added dropwise over 30 minutes. After stirring for a further 30 minutes, the methanol was removed in vacuo and the residue was dissolved in chloroform (40 ml) and saturated aqueous sodium hydrogen carbonate solution (40 ml). The separated chloroform layer was dried (Na$_2$SO$_4$) and the solvent was removed under reduced pressure. The residue was dissolved in methanol (5 ml) and a solution of oxalic acid (0.42 g) in methanol (5 ml) was added. Filtration gave the amine oxalate salt as colourless crystals (identical to that prepared in Example 1).

EXAMPLE 4

1-[2-(2-Methoxy-5-methyl-4-methylsulphinylphenoxy)ethylamino]-3-(2-methylphenoxy)propan-2-ol maleate salt 1-[2-(2-Methoxy-5-methyl-4-methylsulphinylphenoxy)ethylamino]-3-(2-methylphenoxy)propan-2-ol oxalate (1.1 g) was dissolved in water (10 ml) and then methylene chloride (15 ml) and saturated aqueous sodium hydrogen carbonate solution (5 ml) were added. The organic layer was separated, dried (Na$_2$SO$_4$) and the solvent removed under reduced pressure. The resulting oil was taken up in ethanol (5 ml) and maleic acid (0.29 g) in ethanol (2 ml) was added. Removal of solvent and recrystallisation from isopropanol gave the maleate (0.83 g) as colourless crystals, m.p. 130°-136°.

EXAMPLE 5

1-[2-(2-Methoxy-5-methyl-4-methylsulphinylphenoxy)ethylamino]-3-phenoxypropan-2-ol oxalate salt (a) 1-(2-Chloroacetamido)-3-phenoxypropan-2-ol N,N,N',N'-Tetramethylethylenediamine (2.13 ml) was added to 1-amino-3-phenoxypropan-2-ol (4.72 g) in methylene chloride (150 ml). Chloroacetyl chloride (2.25 ml) was then added dropwise with slight cooling and stirring, the mixture being stirred for 30 minutes at room temperature. The precipitate was filtered off and then the methylene chloride was removed in vacuo. The residue was dissolved in ethyl acetate (150 ml) and filtered. Removal of the ethyl acetate in vacuo gave the chloroamide (6 g) as an orange solid $R_f/E$ 0.30.

(b)

1-[2-(2-Methoxy-5-methyl-4-methylsulphinylphenoxy)acetamido]-3-phenoxypropan-2-ol This was prepared from the phenol of Example 2(b) (3.0 g) and the above chloroamide (4.0 g) by the method of Example 2(c). Chromatography on silica gel eluting with methylene chloride/methanol mixtures (gradient 0 to 5% v/v methanol) gave an oil which on trituration with diethyl ether gave the amide (5.5 g) as a white solid $R_f/E$ 0.24.

(c)

1-[2-(2-Methoxy-5-methyl-4-methylsulphinylphenoxy)ethylamino]-3-phenoxypropan-2-ol oxalate salt This was prepared from the above amide (2.44 g) by the method of Example 2(d). The oxalate salt did not crystallise from methanol and so that solvent was removed and the residue was crystallised from ethanol to give the amine oxalate salt (1.45 g) as colourless crystals, m.p. 153°–155°. Found: C, 54.6; H, 6.05; N, 2.7 $C_{20}H_{27}NO_5S.C_2H_2O_4$ requires C, 54.6; H, 6.05; N, 2.9%.

EXAMPLE 6

1-[2-(2-Methoxy-5-methyl-4-methylsulphonylphenoxy)ethylamino]-3-phenoxypropan-2-ol oxalate salt (a)

1-[2-(2-Methoxy-5-methyl-4-methylsulphonylphenoxy)acetamido]-3-phenoxypropan-2-ol m-Chloroperbenzoic acid (0.6 g) was added to a stirred solution of the amide of Example 5(b) (1.22 g) in chloroform (20 ml). After 16 hours the chloroform solution was washed with a mixture of 10% w/v aqueous sodium sulphite solution (10 ml) and saturated sodium bicarbonate solution (10 ml), dried ($Na_2SO_4$) and the solvent was removed in vacuo. Trituration with diethyl ether afforded the amide (1.1 g) as colourless crystals, m.p. 103°–105°.

(b)

1-[2-(2-Methoxy-5-methyl-4-methylsulphonylphenoxy)ethylamino]-3-phenoxypropan-2-ol oxalate salt The above amide (1.2 g) was reduced by the method of Example 2(d). Crystallisation from methanol gave the amine oxalate salt (0.75 g) as colourless crystals, m.p. 178°–179°. Found: C, 52.6; H, 5.8; N, 2.7; $C_{20}H_{27}NO_6S.C_2H_2O_4$ requires C, 52.9; H, 5.85; N, 2.8%.

EXAMPLE 7

1-[2-(2-Methoxy-5-methyl-4-methylsulphonylphenoxy)ethylamino]-3-(2-methylphenoxy)propan-2-ol oxalate salt (a)

1-[2-(2-Methoxy-5-methyl-4-methylsulphonylphenoxy)acetamido]-3-(2-methylphenoxy)propan-2-ol The sulphoxide of Example 2(c) (2.85 g) was oxidised by the method of Example 6(a) to give the amide (2.8 g) as colourless crystals, m.p. 75°–79°.

(b)

1-[2-(2-Methoxy-5-methyl-4-methylsulphonylphenoxy)ethylamino]-3-(2-methylphenoxy)propan-2-ol oxalate salt Borane-tetrahydrofuran complex (22 ml of 1 M solution in tetrahydrofuran) was addes dropwise with stirring at 0° to the above amide (2.5 g) in dry tetrahydrofuran (50 ml). After heating for 2 hours at reflux, the mixture was cooled and 6 N hydrochloric acid (15 ml) was added Tetrahydrofuran (60 ml) was distilled off at atmospheric pressure and then water (20 ml) added to the cooled solution. The solution was basified with solid sodium hydroxide and extracted with chloroform (2×50 ml). The combined organic extracts were dried ($Na_2SO_4$) and the solvent removed in vacuo. The residue was dissolved in methanol (20 ml) and a solution of oxalic acid (0.65 g) in methanol added. Filtration gave the amin oxalate salt (2.4 g) as colourless crystals, m.p. 189°–192°. Found: C, 53.4; H, 6.3; N, 2.7; $C_{21}H_{29}NO_6S.C_2H_2O_4$ requries C, 53.8; H, 6.1; N, 2.7%

EXAMPLE 8

1-[2-(8-Methoxy-2,3,4,5-tetrahydro-1-benzothiepin-7-oxy)ethylamino]-3-(2-methylphenoxy)propan-2-ol S-oxide oxalate salt (a)

7-Hydroxy-8-methoxy-2,3,4,5-tetrahydro-1-benzothiepin-1-oxide and
8-Hydroxy-7-methoxy-2,3,4,5-tetrahydro-1-benzothiepin-1-oxide Sodium hydride (8.8 g of a 50% w/w dispersion in oil) was added over 30 minutes to a solution of ethanethiol (20.8 g) in dry dimethylformamide at 0°. After evolution of hydrogen had ceased additional ethanethiol (8.8 ml) was added followed by 7,8-dimethoxy-2,3,4,5-tetrahydro-1-benzothiepin-1-oxide. The mixture was heated at reflux for 3 hours, cooled and the solvent was removed in vacuo. The residue was taken up in water (100 ml) and extracted with diethyl ether (2×100 ml). The aqueous solution was acidified with conc. hydrochloric acid, saturated with solid sodium chloride and extracted with chloroform (2×100 ml). The organic extract was dried ($Na_2SO_4$) and the solvent was removed in vacuo to give a cream coloured solid. This material was chromatographed on a silica gel column eluting with methylene chloride/methanol mixtures (gradient 0 to 3% v/v methanol) to give the 7-hydroxybenzothiepin (20.7 g), m.p. 165°–166°. Further elution of the column gave, after recrystallisation from methanol, the isomeric 8-hydroxybenzothiepin (2.25 g), m.p. 173°–175°.

(b)

1-[2-(8-Methoxy-2,3,4,5-tetrahydro-1-benzothiepin-7-oxy)acetamido]-3-(2-methylphenoxy)propan-2-ol S-oxide This was prepared from the above 7-hydroxybenzothiepin (2.26 g) and the chloroamide of Example 2(a) (2.7 g) by the method of Example 2(c) affording the amide (4 g) as a buff coloured foam. $R_f E$ 0.27.

(c)

1-[2-(8-Methoxy-2,3,4,5-tetrahydro-1-benzothiepin-7-oxy)ethylamino]-3-(2-methylphenoxy)propan-2-ol S-oxide oxalate salt The above amide (4 g) was reduced by the method of Example 2(d) to give the amine oxalate salt (1.3 g) as colourless crystals, m.p. 100°–105°. Found: C, 55.6; H, 6.5; N, 2.6; $C_{23}H_{31}NO_5S.C_2H_2O_4.H_2O$ requries C, 55.4; H, 6.5; N, 2.6%.

EXAMPLE 9

1-[2-(7-Methoxy-2,3,4,5-tetrahydro-1-benzothiepin-8-oxy)ethylamino]-3-(2-methylphenoxy)propan-2-ol S-oxide oxalate salt (a)

1-[2-(7-Methoxy-2,3,4,5-tetrahydro-1-benzothiepin-8-oxy)acetamido]-3-(2-methylphenoxy)propan-2-ol S-oxide This was prepared from the 8-hydroxybenzothiepin of Example 8(a) (2.6 g) and the chloroamide of Example 2(a) (3.07 g) by the method of Example 2(c) affording the amide (4.4 g) as an orange oil. $R_f E$ 0.33.

(b)

1-[2-(7-Methoxy-2,3,4,5-tetrahydro-1-benzothiepin-8-oxy)ethylamino]-3-(2-methylphenoxy)propan-2-ol S-oxide oxalate salt The above amide (4.4 g) was reduced by the method of Example 2(d) to give the amine oxalate salt (1.1 g) as a colourless solid after three crystallisations from ethanol, m.p. 130°–133°. Found: C, 55.5; H, 6.3; N, 2.55; $C_{23}H_{31}NO_5S.C_2H_2O_4.H_2O$ requires, C, 55.4; H, 6.5; N, 2.6%.

EXAMPLE 10

1-[2-(2,5-Dimethoxy-4-methylsulphinylphenoxy)ethylamino]-3-(2-methylphenoxy)propan-2-ol oxalate salt (a) 2,5-Dimethoxy-4-thiocyanatophenol Bromine (8 g, 2.5 ml) in glacial acetic acid (10 ml) was added dropwise with vigorous stirring over 15 minutes to a mixture of ammonium thiocyanate (8 g), 2,5-dimethoxyphenol (7.7 g), and glacial acetic acid (50 ml) kept at 15°–20°. The mixture was left at room temperature for 30 minutes and then poured into water (400 ml). A solid separated which was filtered off, washed with water and dried in vacuo to give the thiocyanatophenol (7 g). $R_f E$ 0.36.

(b) 2,5-Dimethoxy-4-(methylthio)phenol

The above thiocyanatophenol (7.0 g), triphenylphosphine (8.7 g) and dry methanol (50 ml) were heated at reflux under nitrogen for 2 hours. The mixture was cooled and the methanol removed in vacuo. The resulting oil was column chromatographed on silica gel eluting with diethyl ether/petroleum ether (b.p. 40°–60°) mixtures (gradient 10 to 50% v/v diethyl ether) to give the phenol (5.6 g) as a white solid. $R_f C$ 0.34.

(c)

1-[2-(2,5-Dimethoxy-4-(methylthio)phenoxy)acetamido]-3-(2-methylphenoxy)propan-2-ol Sodium hydride (0.7 g of a 50% w/w dispersion in oil) was added to a solution of the above phenol (2.8 g) in dry dimethylformamide (50 ml). Once evolution of hydrogen had ceased, the chloroamide of Example 2(a) (3.75 g) was added and the mixture was heated at 100° for 1 hour. The solvent was removed in vacuo and the residue dissolved in ethyl acetate (100 ml) and 2 N sodium hydroxide solution (100 ml) added. The organic layer was washed once more with 2 N sodium hydroxide solution and the aqueous extracts were washed once with ethyl acetate. The combined organic extracts were dried ($Na_2SO_4$) and the solvent was removed in vacuo. Trituration with diethyl ether afforded the crystalline amide (3.6 g). $R_f E$ 0.49.

(d)

1-[2-(2,5-Dimethoxy-4-methylsulphinylphenoxy)ethylamino]-3-(2-methylphenoxy)propan-2-ol oxalate salt The above amide (2.1 g) was reduced with borane as in Example 7(b). The amine free base was obtained as a pink solid. This was dissolved in methanol (35 ml), cooled to 0°, and then, with vigorous stirring, peracetic acid (5 ml of a 1 M solution in methanol freshly made from 40% w/w peracetic acid in acetic acid) was added dropwise over 30 minutes. After stirring for a further 30 minutes, the methanol was removed in vacuo and the residue dissolved in chloroform and saturated aqueous sodium hydrogen carbonate solution. The separated chloroform layer was dried ($Na_2SO_4$) and the solvent removed. The residue was dissolved in methanol and oxalic acid (0.45 g) in methanol was added. Filtration gave the amine oxalate salt (1.5 g) as colourless crystals, m.p. 185°–187°. Found: C, 53.55; H, 6.2; N, 2.8: $C_{21}H_{29}NO_6S.C_2H_2O_4$ requires, C, 53.8; H, 6.1; N, 2.7%.

EXAMPLE 11

1-[2-(3,4-Dihydro-6-methoxy-2H-1-benzothiopyran-7-oxy)ethylamino]-3-(2-methylphenoxy)propan-2-ol S-oxide oxalate salt (a)
7-Hydroxy-6-methoxy-2,3-dihydro-1-benzothiopyran-4-one This was prepared from 2,3-dihydro-6,7-dimethoxy-1-benzothiopyran-4-one (4.5 g) by the method of Example 2(b)(i). Recrystallisation from ethanol gave the pyranone (1.7 g) as colourless crystals, m.p. 177°–179°.

(b)
3,4-Dihydro-7-hydroxy-6-methoxy-2H-1-benzothiopyran

Anhydrous aluminium chloride (0.94 g) in dry tetrahydrofuran (5 ml) was added carefully to a suspension of lithium aluminium hydride (0.135 g) in dry tetrahydrofuran (5 ml). The above pyranone (0.45 g) in dry tetrahydrofuran (5 ml) was then added over 15 minutes and the mixture then heated at reflux for 30 minutes. After cooling, ethyl acetate (30 ml) and 10% v/v aqueous sulphuric acid (30 ml) were added. The organic layer was separated, dried ($Na_2SO_4$) and the solvent removed in vacuo. Column chromatography of the resulting oil on silica gel eluting with methylene chloride gave the pyran (0.3 g) as an oil. R$_f$G 0.82.

(c)
1-[2-(3,4-Dihydro-6-methoxy-2H-1-benzothiopyran-7-oxy)acetamido]-3-(2-methylphenoxy)propan-2-ol This was prepared from the above pyran (1.65 g) and the chloroamide of Example 2(a) (2.4 g) by the method of Example 2(c) affording the amide (3.2 g). Purification was achieved by column chromatography on silica gel eluting with methlene chloride/methanol mixtures (gradient 0 to 5% v/v methanol). R$_f$G 0.55.

(d)
1-[2-(3,4-Dihydro-6-methoxy-2H-1-benzothiopyran-7-oxy)ethylamino]-3-(2-methylphenoxy)propan-2-ol S-oxide oxalate salt The above amide (3.2 g) was reduced with borane and oxidised with peracetic acid by the method of Example 10 (d) to give the amine oxalate salt (2.25 g) as colourless crystals, recrystallised from ethanol, m.p. 177°–180°. Found: C, 56.3; H, 6.2; N, 2.7; $C_{22}H_{29}NO_5S.C_2H_2O_4$ requries C, 56.6; H, 6.1; N, 2.75%.

EXAMPLE 12
1-[2-(2-Methoxy-4-methylsulphinylphenoxy)ethylamino]-3-(2-methylphenoxy)propan-2-ol oxalate salt

(a) 2-Methoxy-4-(methylthio)phenol

2-Methoxy-4-thiocyanatophenol (10.2 g) and triphenylphosphine (14.8 g) in dry methanol (150 ml) were heated at reflux under nitrogen for 2 hours. Removal of solvent in vacuo followed by column chromatography on silica gel eluting with diethyl ether/petroleum ether (bp 40°–60°) mixtures (gradient 10 to 50% v/v diethyl ether) gave the phenol as a white solid, m.p. 47°–49°.

(b)
1-[2-(2-Methoxy-4-(methylthio)phenoxy)acetamido]-3-(2-methylphenoxy)propan-2-ol This was prepared from the above phenol (7.35 g) and the chloroamide of Example 2(a) (11.13 g) by the method of Example 10 (c). Column chromatography of the product on silica gel eluting with methylene chloride/methanol mixtures (gradient 0 to 5% v/v methanol) gave the amide (10.0 g) as a pake pink solid. R$_f$E 0.52.

(c)
1-[2-(2-Methoxy-4-methylsulphinylphenoxy)acetamido]-3-(2-methylphenoxy)propan-2-ol m-Chloroperbenzoic acid (1.37 g) in chloroform (30 ml) was added slowly to a chilled, stirred solution of the above amide (3 g) in chloroform (50 ml). After stirring for 30 minutes, this solution was washed with 10% w/v aqueous sodium sulphite, saturated aqueous sodium hydrogen carbonate solution, and brine and then dried ($Na_2SO_4$). Evaporation of solvent in vacuo gave the sulphinylamide (3.5 g) as a colourless oil. R$_f$E 0.65.

(d)
1-[2-(2-Methoxy-4-methylsulphinylphenoxy)ethylamino]-3-(2-methylphenoxy)propan-2-ol oxalate salt The above sulphinylamide (3.34 g) was reduced with sodium borohydride/acetic acid by the method of Example 2(d). The amine free base was column chromatographed on silica gel eluting with methylene chloride/methanol (gradient 0 to 5% v/v methanol) and the oxalate formed in the usual way. The amine oxalate salt (0.6 g) was obtained as colourless crystals, m.p. 132°–135°, Found: C, 54.1; H, 6.1; N, 2.8; $C_{20}H_{27}NO_5S.C_2H_2O_4.\frac{1}{2}H_2O$ requires C, 53.65; H, 6.1; N, 2.8%.

EXAMPLE 13
1-[2-(2-Methoxy-4-methylsulphonylphenoxy)ethylamino]-3-(2-methylphenoxy)propan-2-ol oxalate salt

(a)
1-[2-(2-Methoxy-4-methylsulphinylphenoxy)acetamido]-3-(2-methylphenoxy)propan-2-ol The amide of Example 12(b) (3.0 g) was oxidized by the method of Example 6(a) to give the sulphonylamide (2.5 g) as a white solid. R$_f$E 0.39.

(b)
1-[2-(2-Methoxy-4-methylsulphonylphenoxy)ethylamino]-3-(2-methylphenoxy)propan-2-ol oxalate salt The above sulphonylamide (2.0 g) was reduced with borane by the method of Example 7 to give the amine oxalate salt (1.6 g) as colourless crystals, m.p. 162°–165°. Found: C, 52.3; H, 5.8; N, 2.7; $C_{20}H_{27}NO_6.C_2H_2O_4.\frac{1}{2}H_2O$ requires C, 52.0; H, 5.95; N, 2.75%.

EXAMPLE 14
1-[2-(2-Methoxy-5-methyl-4-methylsulphinylphenoxy)-1-methylethylamino]-3-(2-methylphenoxy)propan-2-ol oxalate salt

(a)
1-(2-Methoxy-5-methyl-4-methylsulphinylphenoxy)-2-propanone

Potassium iodide (0.075 g) was added to a stirred solution of chloroacetone (3 ml) in dry acetone (3.5 ml) and the mixture was stirred for 16 hours. 2-Methoxy-5-methyl-4-methylsulphinylphenol (5.0 g) and potassium carbonate (0.85 g) were heated at reflux with stirring in dry acetone (25 ml). The chloroacetone/potassium iodide solution and potassium carbonate (3.4 g) were then added in four equal portions over 2 hours. The mixture was heated at reflux for a further 2 hours, cooled and filtered, the filter cake being washed well with acetone. The acetone was removed under reduced pressure and the residue chromatographed on a column of silica gel eluting with methylene chloride/methanol mixtures (gradient I to 3% v/v methanol). Trituration with diethyl ether gave the ketone (4.6 g) as colourless crystals, m.p. 104°–106°.

(b)
1-[2-(2-Methoxy-5-methyl-4-methylsulphinylphenoxy)-1-methylamino]-3-(2-methylphenoxy)propan-2-ol oxalate salt The above ketone (2.56 g) and 1-amino-3-(2-methylphenoxy)propan-2-ol (1.8 g) were heated at reflux for 2 hours in ethanol (25 ml) containing molecular sieves (4A ⅛" pellets Linde Air Products). The solution was filtered and the ethanol was removed under reduced pressure. The residue was dissolved in methanol (25 ml) and sodium borohydride (0.75 g) was added with stirring keeping the temperature below 25°. After a further hour stirring at room temperature, the mixture was poured onto ice (50 g) and then acidified with concentrated hydrochloric acid. The solution was basified with solid sodium carbonate and extracted twice with chloroform (50 ml). The combined organic extracts were dried (Na₂SO₄) and the solvent evaporated under reduced pressure. Column chromatography of the residue on silica gel eluting with methylene chloride/methanol mixtures (gradient 0 to 5% v/v methanol) gave the amine as a colourless oil. The oxalate salt was prepared in methanol with oxalic acid (0.23 g). The methanol was removed under reduced pressure and the oxalate salt taken up in hot isopropanol. The oxalate was obtained as a semicrystalline solid by decanting off the isopropanol. Trituration with diethyl ether gave the amine oxalate salt (0.45 g) as a white solid, m.p. 75°–82°.

EXAMPLE 15

1-[2-(8-Methoxy-2,3,4,5-tetrahydro-1-benzothiepin-7-oxy)ethylamino]-3-(2-methylphenoxy)propan-2-ol S,S-dioxide oxalate salt (a)

1-[2-(8-Methoxy-2,3,4,5-tetrahydro-1-benzothiepin-7-oxy)acetamido]-3-(2-methylphenoxy)propan-2-ol S,S-dioxide The amide of Example 8(b) (3.6 g) was oxidised by the method of Example 6(a) to give the desired amide (3.7 g) as an orange foam. $R_f/E$ 0.71.

(b)

1-[2-(8-Methoxy-2,3,4,5-tetrahydro-1-benzothiepin-7-oxy)ethylamino]-3-(2-methylphenoxy)propan-2-ol, S,S-dioxide oxalate salt The above amide (3.7 g) was reduced by the method of Example 7(b) to give the amine oxalate salt (2.55 g) as colourless crystals, m.p. 171°–178°. Found: C, 55.3; H, 6.2; N, 2.5; $C_{23}H_{31}NO_6S.C_2H_2O_4$ requires C, 55.6; H, 6.2; N, 2.6%

EXAMPLE 16

1-[2-(2-Methoxy-5-methyl-4-methylsulphinylphenoxy)-ethylamino]-3-(2-methylphenoxy)propan-2-ol maleate salt (a)

1-Bromo-2-[2-methoxy-5-methyl-4-(methylthio)-phenoxy]ethane

A solution of sodium hydroxide (21 g) in water (75 ml) was added to 2-methoxy-5-methyl-4-methylsulphinylphenol (21 g), dibromoethane (160 ml) and benzyltriethylammonium chloride (1.26 g) and the resultant mixture heated at 60° for 18 hours. After cooling, water (50 ml) was added. The organic layer was separated, the aqueous layer extracted with dibromoethane (2×10 ml). The combined organic extracts were washed with 2 N aqueous sodium hydroxide solution (100 ml) and water (100 ml) and the solvent was evaporated under reduced pressure to give an orange oil, which on trituration with 40°–60° petroleum ether afforded a solid, which was filtered off, washed with further petroleum ether and dried in vacuo. The crude mono-ether (29.24 g), m.p. 66°–67° was used without further purification in the next stage. (A sample purified by column chromatography on Florisil eluting with dichloromethane followed by crystallisation from diethyl ether/40°–60° petroleum ether (1:3 v/v) had m.p. 72°–73°).

(b)

1-[2-(2-Methoxy-5-methyl-4-(methylthio)phenoxy)ethylamino]-3-(2-methylphenoxy)propan-2-ol A solution of sodium hydroxide (9.3 g) in water (20 ml) was added to the above crude mono-ether (27 g), 5-(2-methylphenoxymethyl)oxazolidin-2-one (24 g), benzyltriethylammonium chloride (1.5 g) in dichloromethane (80 ml) and the mixture stirred at reflux for 24 hours. Additional oxazolidinone (3 g) and benzyltriethylammonium chloride (0.5 g) were added. After a total of 48 hours reflux the mixture was cooled, water (50 ml) was added. The organic layer was separated, washed with water (50 ml) and the solvent was evaporated to yield a yellow oil. The oil was refluxed with a mixture of sodium hydroxide (10.4 g) and ethanol (200 ml) for 24 hours. The ethanol was evaporated under reduced pressure to afford a gum, which on trituration with ethanol/water (1:3 v/v; 100 ml) gave a white solid. The solid was collected, washed with ethanol/water (1:3 v/v; 50 ml) and water (2×50 ml), slurried with diethyl ether/40°–60° petroleum ether (1:1 v/v; 2×50 ml), washed with further diethyl ether/petroleum ether (50 ml) followed by petroleum ether (50 ml). The solid was dissolved in dichloromethane (200 ml), the solution washed with water (50 ml), dried (Na₂SO₄) and evaporated to afford a yellow oil which rapidly crystallised to give the amine sulphide as an off-white solid (25.15 g) m.p. 92°–94°.

(c)

1-[2-(2-Methoxy-5-methyl-4-methylsulphinylphenoxy)ethylamino]-3-(2-methylphenoxy)propan-2-ol maleate salt Peracetic acid (5.6 ml of 40% w/v peracetic acid in acetic acid) in methanol (5.5 ml) was added dropwise over 1 hour to a stirred solution of the above amine sulphide (10.9 g) at ~0° C. After stirring for a further ½ hour 0.5 M aqueous sodium metabisulphite solution (10 ml) was added. The solution was basified to pH 7 by the addition of saturated aqueous sodium bicarbonate solution and the extracted with chloroform (3×50 ml). The combined extracts were washed with aqueous sodium metabisulphite solution and brine, dried (MgSO₄) and evaporated under reduced pressure to afford an oil (12.7 g). 10.7 g of the oil was taken up in hot ethanol (25 ml) and maleic acid (3.0 g) in hot ethanol (15 ml) was added and the mixture allowed to cool. Diethyl ether (30 ml) was slowly added. After standing at 0° for 24 hours the mixture was filtered to afford the maleate salt (8.3 g) as a cream solid (identical to that prepared in Example 4).

Peripheral vasodilator agents are used clinically to lower blood pressure in hypertensive patients. However, the fall in blood pressure produced by these compounds is usually associated with reflex physiological changes which produce undesirable side effects such as increases in heart rate (tachycardia) and plasma renin levels. These side effects have been eliminated clinically by the co-administration of a β-adrenoreceptor antagonist with the antihypertensive vasodilator agent. This combination drug therapy obviously suffers from disadvantages in that the doses of the two compounds must be individually regulated and also the risk of patient error is increased when self-administering more then one drug entity. These problems of patient compliance associated with such therapy would be alleviated by using a single dose drug entity which has both vasodilator and β-adrenoreceptor antagonist properties present in the same molecule.

Pharmacological evaluation of the compounds of the invention has demonstrated that they possess β-adrenoreceptor antagonist activity and, unlike classical β-blocking agents, produce falls in blood pressure after acute administration due to an additional vasodilator action. These compounds would therefore be therapeutically useful in the treatment of hypertension and not produce the intrinsic side effects of currently used vasodilator agents.

β-Adrenoreceptor blocking properties of compounds of the invention have been investigated in an in vitro test by assessing the degree of antagonism of the positive chronotropic responses to (−)-isoprenaline in isolated guinea-pig right atria (Harms, 1976, J. Pharmacol. Exp. Ther., 199, 329). Competitive β-adrenoreceptor blocking potencies of compounds have been expressed in terms of their $pA_2$ values (Van Rossum, 1963, Arch. Int. Pharmacodyn., 143, 299) and results of 4 examples are listed in Table 1. β-Adrenoreceptor blocking $pA_2$ values for the standard antagonists (±)-propranolol and (±)-tolamolol are also shown in the Table. Tolamolol is the approved name for 1-[2-(4-carbamoylphenoxy)ethylamino]-3-(2-methylphenoxy)propan-2-ol. Tolamolol which is covered by the above mentioned British Pat. No. 1,245,148 was selected from the compounds covered by the patent for clinical evaluation in man.

Antihypertensive activities of test compounds after oral administration have been determined by calculating the percentage falls in mean arterial blood pressure in groups of DOCA rats (prepared by the method of Stanton & White, 1966, Arch. Int. Pharmacodyn. Ther., 154, 351) with chronically implanted aortic cannulae (Weeks & Jones, 1960, Proc. Exp. Biol. Med., 104, 646). The maximum percentage changes in mean arterial blood pressure produced by four examples as well as the standard β-adrenoreceptor antagonists (±)-propranolol and (±)-tolamolol are shown in the Table. As an indication of the duration of action of these compounds, the percentage changes observed 1, 2, 3 and 5 hours after dosage have been summated.

TABLE 1

| Compound | β-Adrenoreceptor Antagonist Activity in Isolated Guinea-Pig Atria $pA_2$ value against chronotropic responses of isoprenaline | Antihypertensive Activity in DOCA hypertensive rats | |
|---|---|---|---|
| | | oral dose mg/kg | maximal percent changes in MABP | Summation of percent changes |
| (±)-Propranolol | 7.71 | 5 | +10, −5 | +15, −6 |
| | | 50 | +11 | +38 |
| (±)-Tolamolol | 7.77 | 50 | −20 | −47 |
| | | 100 | −30 | −88 |
| Example 1 | 6.42 | 50 | −37 | −137 |
| | | 100 | −47 | −170 |
| Example 6 | 6.72 | 100 | −35 | −127 |
| Example 8 | 7.54 | 100 | −43 | −161 |

TABLE 1-continued

| Compound | β-Adrenoreceptor Antagonist Activity in Isolated Guinea-Pig Atria $pA_2$ value against chronotropic responses of isoprenaline | Antihypertensive Activity in DOCA hypertensive rats | |
|---|---|---|---|
| | | oral dose mg/kg | maximal percent changes in MABP | Summation of percent changes |
| Example 10 | 7.53 | 100 | −36 | −131 |

(a) The $pA_2$ value of an antagonist is defined as the negative logarithm of the molar concentration of a compound which displaces the control dose-response curve of an agonist to the right in a parallel manner by a factor of two. The values in this table are the mean of 4–8 experiments.
(b) DOCA = Desoxycorticosterone acetate.
(c) MABP = Mean arterial blood pressure. Negative values represent falls in blood pressure and conversely positive values increases in blood pressure. The values of maximum percent changes are mean values taken from groups of 5–7 DOCA hypertensive rats.
(d) Values in the final column represent duration of action of the relative increases and decreases in blood pressure with the respective treatments. Group mean percent changes are added together for the times of 1, 2, 3 and 5 hours after oral dosage. Larger values represent longer durations of action.

From the Table it can be seen that (±)-propranolol and (±)-tolamolol were the most potent β-adrenoreceptor antagonists tested in vitro and the compounds of Examples 8 and 10 were 1.5 times less active than (±)-propranolol. (±)-Propranolol was approximately 10 and 20 times more potent as an antagonist than the compounds of Examples 6 and 1 respectively.

Oral administration of a small dose of (±)-propranolol (5.0 mg/kg) produced a small increase in mean blood pressure followed by a non-significant transient fall. (±)-Propranolol (50 mg/kg, p.o.) produced a long-lasting increase in blood pressure. Both doses of (±)-propranolol decreased heart rate. (±)-Tolamolol produced falls in blood pressure which were relatively transient. This effect on blood pressure was of a shorter duration than the bradycardia noted with (±)-tolamolol. These results indicate that β-adrenoreceptor antagonists do not markedly decrease blood pressure in DOCA hypertensive rats and therefore compounds which possess β-adrenoreceptor antagonist properties and lower blood pressure in this animal model do so by an additional vasodilator action. The Table indicates that all four examples of the invention lower blood pressure to a greater extent than (±)-tolamolol both in terms of maximum effect and duration of action. All four examples lowered heart rate in conjunction with the blood pressure effects and the time course of these two effects were similar. Therefore, no reflex increases in heart rate, which might have been expected in response to the marked fall in blood pressure, were noted with these compounds.

In the compound of Example 1 (Formula III; $R^2=CH_3SO$, $R^3=R^4=CH_3$) the $CH_3SO$ group is in the para position in one ring (relative to the oxygen bridge) with a methyl group in the ortho position in the other ring (relative to the oxygen bridge).

Table 2 gives results using the above tests for this compound and shows the deleterious effects (in Examples A and B) of having the $CH_3SO$ group in the ortho or meta positions and (in Examples C and D) of having the methyl group in the meta or para positions respectively. The compounds of Examples A, B, C and D are outside the scope of the present invention.

TABLE 2

| Example | | | | β-Antag. $pA_2$ | MABP |
|---|---|---|---|---|---|
| 1 | 2-OMe | 4-SOMe | 5-Me; 2-Me | 6.42 | −170(−47) |

TABLE 2-continued

| Example | | | | β-Antag. pA₂ | MABP |
|---|---|---|---|---|---|
| A | 2-OMe | 4-Me | 5-SOMe; | 2-Me | 5.50 | −127(−37) |
| B | 2-SOMe | 4-OMe | H; | 2-Me | NT | toxic |
| C | 2-OMe | 4-SOMe | 5-Me; | 3-Me | pD′₂ = 4.3 | −23(−8) |
| D | 2-OMe | 4-SOMe | 5-Me; | 4-Me | 5.93 | −82(−23) |

(a) The antihypertensive results followed an oral dose of 100 mg/kg. Values in the final column are summation of percent changes with, in brackets the maximum percent changes.
(b) NT = Not tested.
(c) In the β-adrenoreceptor antagonism test the interaction between Example C and isoprenaline was non-competitive in nature. pD′₂ = Negative logarithm of the molar concentration which causes the maximum response of the agonist to be depressed by 50%.
(d) With Example B in the antihypertensive test at an oral dose of 100 mg/kg 5 of the 6 test rats died.

The invention also includes the use of a compound of formula II or formula III, or a non-toxic salt thereof in the treatment of hypertension and a method of treating hypertension which comprises administering to a patient an antihypertensive effective amount of a compound of formula II or formula III, or a non-toxic salt thereof.

The pharmaceutical compositions may be in a form suitable for oral, rectal or parenteral administration. Such oral compositions may be in the form of capsules, tablets, granules or liquid preparations such as elixirs, syrups or suspensions.

Tablets contain a compound of formula II or formula III, or a non-toxic salt thereof in admixture with excipients which are suitable for the manufacture of tablets. These excipients may be inert diluents such as calcium phosphate, microcrystalline cellulose, lactose, sucrose or dextrose; granulating and disintegrating agents such as starch; binding agents such as starch, gelatine, polyvinylpyrrolidone or acacia; and lubricating agents such as magnesium stearate, stearic acid or talc.

Compositions in the form of capsules may contain the compound or a non-toxic salt thereof mixed with an inert solid diluent such as calcium phosphate, lactose or Kaolin in a hard gelatine capsule.

Compositions for parenteral administration may be in the form of sterile injectable preparations such as solutions or suspensions in for example water, saline or 1,3-butanediol.

For the purposes of convenience and accuracy of dosing the compositions are advantageously employed in a unit dosage form. For oral administration the unit dosage form contains from 10 to 500 mg, preferably 50 to 300 mg of the compound of formula II or formula III, or a non-toxic salt thereof. Parenteral unit dosage forms contain from 1 to 50 mg of the compound of formula II or formula III, or a non-toxic salt thereof per 1 ml of the preparation.

The invention is further illustrated by the following Examples of compositions in which all parts are by weight.

EXAMPLE I

A mixture of equal parts of the compound of Example 4 and microcrystalline cellulose together with 1% of magnesium stearate is compressed into tablets. Conveniently the tablets are of such a size as to contain 50, 100 or 200 mg of the active ingredient.

EXAMPLE II

A mixture of equal parts of the compound of Example 4 and spray dried lactose together with 1% magnesium stearate is filled into hard gelatin capsules. The capsules may conveniently contain 50 or 100 mg of the active ingredient.

We claim:

1. A compound of the formula:

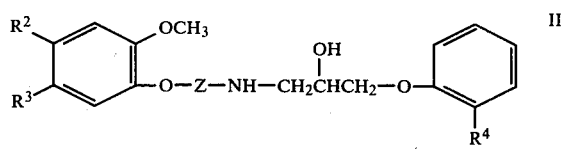

wherein
R² is CH₃SO or CH₃SO₂;
R³ is hydrogen, methyl or methoxy; or
R² and R³ are together —S(O)ₘ(CH₂)₄— when S is attached at R² or
—(CH₂)ₙS(O)ₘ— when S is attached at R³ (where m=1 or 2 and n=3 or 4);
R⁴ is hydrogen or alkyl C₁₋₄;
Z is —(CH₂)₂— or

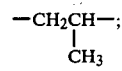

and their non-toxic salts.

2. A compound of the formula:

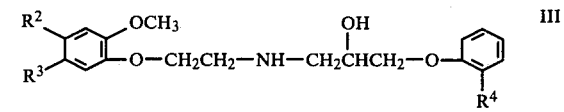

wherein
R² is CH₃SO or CH₃SO₂;
R³ is hydrogen, methyl or methoxy; or
R² and R³ are together —S(O)ₘ(CH₂)₄— when S is attached at R² or
—(CH₂)ₙS(O)ₘ— when S is attached at R³ (where m=1 or 2 and n=3 or 4);
R⁴ is hydrogen or methyl; and their non-toxic salts.

3. The compound of claim 1 which is 1-[2-(2-Methoxy-5-methyl-4-methylsulphinylphenoxy)ethylamino]-3-(2-methylphenoxy)propan-2-ol.

4. The compound of clam 1 which is 1-[2-(2-Methoxy-4-methylsulphonylphenoxy)ethylamino]-3-phenoxypropan-2-ol.

5. The compound of claim 1 which is 1-[2-(8-Methoxy-2,3,4,5-tetrahydro-1-benzothiepin-7-oxy)ethylamino]-3-(2-methylphenoxy)propan-2-ol S-oxide.

6. The compound of claim 1 which is 1-[2-(2,5-Dimethoxy-4-methylsulphinylphenoxy)ethylamino]-3-(2-methylphenoxy)propan-2-ol.

7. The compound of claim 1 which is 1-[2-(8-Methoxy-2,3,4,5-tetrahydro-1-benzothiepin-7-oxy)ethylamino]-3-(2-methylphenoxy)propan-2-ol S,S, dioxide.

8. A pharmaceutical composition for the relief of hypertension which comprises at least one compound as claimed in claim 1 or a non-toxic salt thereof together with a pharmaceutically acceptable diluent or carrier.

9. A pharmaceutical composition for the relief of hypertension according to claim 8 in unit dosage form for oral administration which contains from 10 to 500 mg of the compound or salt thereof per unit dosage.

10. A method of treating hypertension which comprises administering to a patient an antihypertensive effective amount of a compound as claimed in claim 1 or a non-toxic salt thereof.

* * * * *